US010655134B2

(12) United States Patent
Amann et al.

(10) Patent No.: US 10,655,134 B2
(45) Date of Patent: May 19, 2020

(54) PRODUCTION OF RECOMBINANT EXPRESSION VECTORS

(71) Applicant: Eberhard Karls Universitaet Tuebingen Medizinische Fakultaet, Tuebingen (DE)

(72) Inventors: Ralf Amann, Tuebingen (DE); Hans-Joachim Rziha, Tuebingen (DE)

(73) Assignee: EBERHARD KARLS UNIVERSITAET TUEBINGEN MEDIZINISCHE FAKULTAETGESCHWISTER-SCHOLL-PLATZ, Tuebingen (DE)

( * ) Notice: Subject to any disclaimer, the term of this patent is extended or adjusted under 35 U.S.C. 154(b) by 0 days.

(21) Appl. No.: 15/590,902

(22) Filed: May 9, 2017

(65) Prior Publication Data
US 2017/0240907 A1    Aug. 24, 2017

Related U.S. Application Data

(63) Continuation of application No. PCT/EP2015/075152, filed on Oct. 29, 2015.

(30) Foreign Application Priority Data

Nov. 10, 2014  (DE) .................. 10 2014 116 334

(51) Int. Cl.
| | | |
|---|---|---|
| *C12N 15/64* | (2006.01) | |
| *C07K 14/005* | (2006.01) | |
| *C07K 14/73* | (2006.01) | |
| *C12N 15/10* | (2006.01) | |
| *C12N 15/90* | (2006.01) | |
| *A61K 39/00* | (2006.01) | |
| *A61K 39/12* | (2006.01) | |

(52) U.S. Cl.
CPC .......... *C12N 15/64* (2013.01); *A61K 39/0011* (2013.01); *A61K 39/12* (2013.01); *C07K 14/005* (2013.01); *C07K 14/70514* (2013.01); *C12N 15/1013* (2013.01); *C12N 15/907* (2013.01); *C12N 2760/20134* (2013.01); *C12N 2800/107* (2013.01)

(58) Field of Classification Search
None
See application file for complete search history.

(56) References Cited

U.S. PATENT DOCUMENTS 6,284,541 B1 *   9/2001   Auer .................... C12N 15/907
                                                      435/463

FOREIGN PATENT DOCUMENTS

| WO | WO 2009/066180 A2 | 5/2009 |
| WO | WO 2011/145013 A1 | 11/2011 |

OTHER PUBLICATIONS

Foley, et al. (2000) "A recombinant rabies virus expressing vesicular stomatitis virus glycoprotein fails to protect against rabies virus infection", Proceedings of the National Academy of Science, USA, 97(26): 14608-85. (Year: 2000).*
Lodish, et al. (2000) "Section 7.1 DNA Cloning with Plasmid Vectors", Molecular Cell Biology, 4th Ed., published by WH Freeman, New York, NY, (NIH Bookshelf Article) 8 pages as printed. (Year: 2000).*
Amann et al.: A New Rabies Vaccine Based on a Recombinant Orf Virus (Parapoxvirus) Expressing the Rabies Virus Glycoprotein; Journal of Virology, 2013, 87(3) 1618-1630.
Hoffmann and Wildner: Efficient generation of double heterologous promoter controlled oncolytic adenovirus vectors by a Single homologous recombination step in *Escherichia coli*; BMC Biotechnology 2006, 6:36.
David et al.: Magnetic Cell Sorting Purification of Differentiated Embryonic Stem Cells Stably Expressing Truncated Human CD4 as Surface Marker; Stem Cells 2005; 23:477-482.
Fischer et al.: Novel Recombinant Parapoxvirus Vectors Induce Protective Humoral and Cellular Immunity against Lethal Herpesvirus Challenge Infection in Mice; Journal of Virology, Sep. 2003, p. 9312-9323.
International Search Report for PCT/EP2015/075152, dated Feb. 26, 2016, 7 pages.
International Preliminary Report on Patentability for PCT/EP2015/075152, dated May 16, 2017, 13 pages.

\* cited by examiner

*Primary Examiner* — Robert M Kelly
(74) *Attorney, Agent, or Firm* — Rimon, P.C.

(57) ABSTRACT

The present invention relates to a method for the production of recombinant expression vectors, a kit adapted to carrying out the method, a vector used in the context of the method, a cell containing such vector and the use of the vector.

9 Claims, 6 Drawing Sheets

PRODUCTION OF RECOMBINANT EXPRESSION VECTORS

CROSS-REFERENCES TO RELATED APPLICATIONS

This application is a continuation of the copending international patent application PCT/EP 2015/075152 filed on 29 Oct. 2015 and designating the U.S., which has been published in German, and claims priority from German patent application DE 10 2014 116 344.6 filed on 10 Nov. 2014. The entire contents of these prior applications are incorporated herein by reference.

BACKGROUND OF THE INVENTION

Field of the Invention

The present invention relates to a method for the production of recombinant expression vectors, a kit adapted to carry out the method, a vector used in connection with the method, a cell containing said vector, and the use of the vector.

Related Prior Art

A central subject matter of molecular cloning is the production of recombinant nucleic acid molecules. For this purpose, a desired nucleic acid molecule, usually a DNA fragment or a gene, is integrated in a so-called vector or a "gene shuttle", such as for example a plasmid or a viral vector. An object of cloning is to amplify the integrated DNA fragment or gene to examine its properties or to further use them in follow-up processes. After a multiplication the vector can be isolated and a multiple of the initially used DNA fragment can be gained. Alternatively, cells into which a DNA fragment was introduced via a vector by means of cloning, can express a gene product encoded by the DNA fragment, e.g. a protein or peptide. Such a vector is also referred to as expression vector.

Standardized experiments for the cloning of any DNA fragment essentially comprise the following seven steps: (1) selection of the host organism and the cloning vector, (2) production of the vector, (3) production of the DNA to be cloned, (4) generation of recombinant DNA, (5) introduction of the recombinant DNA into the host organism, (6) selection of organisms containing the recombinant DNA, (7) screening for clones with the desired cloned DNA and/or the desired biological properties.

One of the time-limiting factors in the production of recombinant (expression) vectors is the selection of such clones which express the introduced gene product. One of the frequently used methods is the so-called blue white selection. The objective of the blue white selection is the identification of cells which express the desired introduced gene. As a rule, for the blue white selection specific plasmids are used as vectors, which contain at the position for the insertion of the "gene of interest" into the plasmid at the so-called 'multiple cloning site' the gene for a β-galactosidase, the so-called lacZ gene. The gene for the galactosidase is used as reporter gene. By the introduction of the gene of interest into the multiple cloning site the galactosidase is inactivated. By this, after a transformation of the plasmids the transgenic organisms, in contrast to the nontransgenic organisms, do not contain a functional galactosidase. The galactosidase can cleave the yellow dye 'X-gal' into a blue dye and galactose. When using X-gal culture medium about half an hour after the induction a blue dye is produced by the galactosidase contained in the cells. However, in the transgenic cells the galactosidase is inactivated in which case they remain undyed and can be isolated with reference to their lack of dye.

This selection method is very time-consuming and labor-intensive. It is not unusual that in particular for the production of recombinant virus based expression vectors up to 6 to 12 month are required which is, for example, unfavorable for the production of seasonally required or individualized vaccines.

Other methods for the production or selection of recombinant vectors currently used in the state of the art are likewise time-consuming and labor-intensive.

SUMMARY OF THE INVENTION

Against this background an object underlying the invention is to provide a method for the production of recombinant expression vectors which is less labor-intensive and results in the desired recombinant vectors more rapidly than which is currently the case in the presently used methods.

This object is met by a method for the production of recombinant expression vectors, comprising the following steps:

(1) providing a cell population containing a starting vector, said cell population expressing a first gene product encoded by the starting vector in such a way that it is accessible to a first binding molecule binding to said first gene product, wherein in the starting vector the coding nucleotide sequence for said first gene product is upstreamly and downstreamly flanked by first recombination nucleotide sequences;

(2) transfecting the cell population obtained from step (1) with a transfer vector encoding a second gene product, wherein in said transfer vector the coding nucleotide sequence for said second gene product is upstreamly and downstreamly flanked by second recombination nucleotide sequences which are homologous to the first recombination nucleotide sequences;

(3) incubation of the cell population obtained from step (2) under conditions which allow the exchange of the coding nucleotide sequence for the first gene product against the coding nucleotide sequence for the second gene product by homologous recombination of said first and second recombination nucleotide sequences and the formation of a recombinant expression vector;

(4) incubation of the cell population obtained from step (3) under conditions which allow the expression of said second gene product, where applicable in such a manner that it is accessible to a second binding molecule which binds to the second gene product, and (5) contacting the cell population obtained from step (4) with said first binding molecule which binds to said first gene product under conditions which allow the formation of complexes of said first binding molecule and first gene products;

(6) separation of complexes of first binding molecule and first gene product from the cell population, and (7) isolation of the recombinant expression vectors from the cell population and/or, where appropriate, (5') contacting the cell population obtained from step (4) with said second binding molecule which binds to the second gene product under conditions which allow the formation of complexes of the second binding molecule and second gene product;

(6') separating the complexes of second binding molecule and second gene product, and (7') isolating the recombinant expression vectors from the complexes of second binding molecule and second gene product.

A "recombinant expression vector" refers to a vector which comprises the coding nucleotide sequence for a desired gene product, such as the second gene product, and which is constructed in such a manner that the coding nucleotide sequence is transcribable into mRNA and subsequently translatable into a gene product. The expression vector according to the invention is generated by recombination events via which the coding nucleotide sequence for the desired gene product is introduced into the expression vector. According to the invention "expression vectors" include so-called plasmid vectors, viral vectors or according to alternative embodiments possibly also bacteriophage vectors, cosmids, phagemids, bacmides and bacs. Plasmid vecotrs are vectors which are obtained from plasmids. Viral vectors refer to modified viruses which can transduce eukaryotic cells, and, by doing so, can introduce foreign genes into the cells. Bacteriophages are viruses which affect bacteria. By the incorporation of cos-sites from λ phages into plasmids so-called cosmids are obtained. A phagemid is a plasmid which carries an origin of replication for single stranded replication of F1 phages. A bacmide is a "shuttle vector" for bacteria and insect cells. Bacs or "bacterial artificial chromosome" are complete virus genomes amplifiable in bacteria. The invention is particular suitable for the production of recombinant viral vectors or recombinant viruses, respectively, such as e.g. recombinant pox viruses, including the parapox viruses (ORFV). For this reason the invention also refers to a method for the production or selection of recombinant viral vectors or recombinant viruses with the indicated steps.

In the method according to the invention the "production" or "producing" also includes the selection or selecting. The invention therefore also relates to a method for the selection of recombinant expression vectors with the indicated steps.

A "starting vector" refers to an expression or cloning vector which encodes the first gene product which can be expressed in the cell of the cell population according to the invention. According to the invention the starting vector can also be referred to as starting expression vector or starting cloning vector. The starting vector can be a linear or circular, a single or double stranded, a DNA or RNA vector.

A "cell population" refers to a group of cells of similar type which are transfectable by the starting and transfer vectors according to the invention. According to the invention the "cells" encompass biological cells of animal, plant or bacterial origin. Alternatively, artificial or minimum cells come into question, such as nanoparticles, liposomes, polymeresomes, microcapsules etc. Preferably according to the invention such cells are employed which naturally do not express the first gene product. It goes without saying that the starting vector can also be provided in several different cell populations. In this respect according to the invention the provision of "at least one" cell population containing a starting vector is included.

A "gene product" according to the invention refers to a nucleic acid encoded molecule. Examples are amino acid sequences, peptides, proteins or protein fragments. The "first" gene product is preferably an entity suitable as a selection marker, for example a foreign or transgene, if applicable, also a starting vector inherent gene product which is not essential for the function of the vector. Preferably the first gene product is such a gene product which the cells naturally do not express. The "second" gene product is preferably a "gene of interest", a foreign or transgene.

According to the invention a "binding molecule" is such a molecule which selectively and specifically binds to the gene product and can form a complex with the latter. Examples for binding molecules which are suited according to the invention include antibodies or immunoglobulins, aptameres, and fragments thereof.

The accessibility of the first and second gene product to a binding molecule can be realized by various kinds. For example, the first and/or second gene product is located on the surface of the cells with an orientation towards the exterior of the cell, e.g. as transmembrane protein. According to a further alternative embodiment the first and/or second gene product is localized on the surface of a virus particle with an orientation into the exterior of the virus, e.g. as virus envelope protein. According to another further alternative embodiment the first and/or second gene product are in soluble form in the cell, the cell is permeabilized or lysed so that the first or second binding molecule can contact the first and/or second gene product.

"Upstreamly" according to the invention means that the recombination nucleotide sequences are located relatively to the coding nucleotide sequences for the first and the second gene product in the direction of the respective 5' terminus. "Downstreamly" according to the invention means that the recombination nucleotide sequences are located relatively to the coding nucleotide sequences for the first and the second gene product in the direction of the respective 3' terminus. The coding nucleotide sequences for the first and the second gene product are, as a consequence, on both sides limited or flanked by recombination nucleotide sequences.

"Transfecting" according to the invention generally means the introduction of a vector, e.g. the transfer vector, into the cells of the cell population. According to the invention this is not restricted to eukaryotic cells. Therefore, transfection also comprises the transduction or the introduction of a vector into prokaryotic cells, e.g. into bacteria cells, such as the cells of *Escherichia coli*. When using viral vectors or recombinant viruses as starting vectors instead of transfecting it is also referred to "infecting" and instead of transfection it is also referred to "infection".

According to the invention a "transfer vector" refers to a transportation vehicle or a "gene shuttle" for introducing the genetic information for the second gene product into the cells of the cell population. The transfer vector can be e.g. a linear or, according to an alternative embodiment, a circular, a single or double stranded, a DNA or RNA vector.

According to the invention "homologous" means that the first recombination nucleotide sequence is identical with or complementary to the second recombination nucleotide sequence to such an extent that homologous recombination can take place. The homology between the first and second recombination nucleotide sequence is in one embodiment of the invention at least 90%, further preferably at least 95%, further preferably at least 99%, and highly preferably 100%.

"Separating" in the steps (6) and (6') includes the spatial separation of the complexes of the first or second binding molecule and the first and/or second gene product from the cell population or remaining cell population, respectively. This separation can take place by means of physical, chemical and biological methods known to the skilled person. Included are flow cytometric methods, the "magnetic cell separation", or "magnetic activated cell sorting" (MASC), and the immunoprecipitation. Alternatively a separation can occur via the density. For this purpose via the first and/or second binding molecule a heavy particle, such as gold or lead, or, alternatively, a light particle, are bound to the complex and subsequently separated from the non-complexed cells via density separation. Also a separation via the size is possible. Here the first and/or second binding molecule is bound to a large entity such as a sphere. The complexes or cells are placed on an sieve. The large complexes cannot pass the sieve and are separated from the small complexes or cells, respectively. Such a system is provided under the name PluriBead®. According to the invention also the use of affinity chromatography methods under the use of a column matrix or the separation in the electrical fields is included, wherein here the first and/or second binding molecules comprise an electrically charged particle.

The method according to the invention can be carried out with the steps (1), (2), (3), (4), (5), (6) and (7). In this branch of the method a so-called "negative selection" is made. This selection is referred to as "negative" because it is selected for a loss of a property, namely for the loss of the first gene product. In step (5) of this branch of the method complexes of the first binding molecule and the first gene product can form. In step (6) these complexes are separated from the cell population. By this such cells or (starting) vectors are separated from the cell population, where no recombination and therefore no exchange of the coding nucleotide sequence for the first against such for the second gene product has taken place. The separated cells largely correspond to such from step (1). The cells of the remaining "cleared up" or depleted cell population however no longer express the first gene product and may therefore not form a complex with the first binding molecule. In the remaining depleted cells by homologous recombination an exchange of the coding nucleotide sequence for the first gene product against the coding nucleotide sequence for the second gene product and, therefore, the formation of the desired recombinant expression vector has taken place. The desired recombinant expression vector is isolated from the cells of the remaining cell population in step (7) by means of methods well known to the skilled person which include the disruption of the cells and the release of the vector.

The method according to the invention can alternatively be carried out with the steps (1), (2), (3), (4), (5'), (6') and (7'). In this branch of the method a so-called "positive selection" is made. The selection is referred to as "positive" because a selection is made for the obtainment of a property, namely for the second gene product. In step (5') of this branch of the method complexes of the second binding molecule and second gene product can form. In step (6') the cells of the cell population are separated from these complexes, where no homologous recombination has taken place and therefore the second gene product is not expressed. The complexes of the second binding molecule and the second gene product contain the desired recombinant expression vector which is isolated in step (7'). According to a preferred embodiment the complexes comprise e.g. recombinant virus particles if, e.g., a viral vector is used as the starting vector and the second gene product was incorporated into the virus particle, from which in step (7') the recombinant expression vector can be isolated. According to another alternative embodiment the complexes comprise cells in which or on which the second gene product is present, and from which in step (7') the recombinant expression vector can be isolated.

After the steps (1), (2), (3) and (4) the steps (5), (6) and (7) and (5'), (6') and (7') can also be carried out in parallel. Alternatively, also at first the steps (5), (6) and (7) and then the steps (5'), (6') and (7') can be carried out or vice versa.

The method according to the invention also allows a combination of negative and positive selection.

If it is completely refrained from a "positive selection" it is not necessary that in step (4) the expression of the second expression product is of such kind that it is accessible to the second binding molecule. The accessibility is thus dispensable which is made clear by the term "where appropriate" or "if applicable". Insofar the steps (5')-(7') are only carried out if in step (4) the expression of the second expression protein is realized in such a manner that it is accessible to the second binding molecule.

By the new production method according to the invention recombinant expression vectors can now be produced within only 1 to 2 weeks in a cost-effective manner. This is in particular advantageous for the production of therapeutically useful gene products which are to be made available within a very short time.

The new production method also allows the production of recombinant bacteria or recombinant cells, for example if the expressed gene product in the cell exerts a specific function.

According to an embodiment of the invention the first gene product is a protein or protein fragment, preferably a membrane protein, further preferably a cell surface protein, and highly preferably CD4.

Here a "protein" or "protein fragment" also includes a peptide or an amino acid sequence. A membrane protein is an entity which is particularly appropriate as a selection marker. By means of the first binding molecules which selectively and specifically bind to the membrane protein such cells can be separated in which no homologous recombination and no formation of the desired recombinant expression vector has taken place. After these cells are removed the desired recombinant expression vector can be isolated from the remaining cells which do not bind to the first binding molecule. In doing so it was realized that "CD4" (cluster of differentiation 4) is an especially suitable selection marker.

According to an embodiment according to the invention the first gene product is a protein which can be detected by means of an imaging method, for example a fluorescence protein. In such a case in step (1) the accessibility for a first binding molecule is dispensable because a negative selection is made for the loss of a protein which is detectable by means of imaging methods, for example for the loss of fluorescence. In step (1) the requirement is obsolete according to which the first gene product is expressed in such a manner that it is accessible to a first binding molecule that binds to the first gene product. An expression in any form whatsoever which results in a functional first gene produce is sufficient. Also the steps (5) to (7) are eliminated because a first binding molecule is not in use. Instead, the following steps (5*) to (7*) are carried out: (5*) subjecting the cell population obtained from step (4) to a fluorescence activated cell sorting (FACS); (6*) separating the fluorescent cells from the cell population, and (7*) isolation of the recombinant expression vectors from the cell population. "Cell population" in step (7*) refers to the "remaining" cell population reduced by the separated cells. The advantages, characteristics, and properties of the method disclosed in the application in connection with the steps (5)-(7) and (5')-(7') apply to this alternative embodiment correspondingly.

According to an embodiment of the method according to the invention in step
(5) the cell population obtained from step (4) is contacted with the binding molecule which binds to the first gene product under conditions which allow the formation of complexes of first binding molecule and cells, and in step (6) said complexes of first binding molecule and cells are separated from cells which do not bind to the first binding molecule (negative cells), and in step (7) the recombinant expression vectors are isolated from the negative cells.

In this embodiment the first gene product is present in a complex with the cells in which the starting vector was introduced so that via the binding of the first binding molecule to the first gene product, which takes place in step (5), in step (6) also the "negative" cells can be separated. Therefore, the first gene product is e.g. a cell associated gene product which is accessible for the binding molecule from outside of the cell. Preferably the first gene product is a membrane protein. In step (7) the desired recombinant expression vectors can be isolated from the remaining cell subpopulation.

According to an embodiment of the method according to the invention after step (6) and before step (7) the following further steps occur:

(6.1) disintegrating the negative cells to obtain a cell lysate which contains the recombinant expression vectors;

(6.2) incubation of the cell lysate obtained from step (6.1) with non-transfected cells under conditions allowing a transfection of the cells with the recombinant expression vectors to obtain a transfected cell population;

(6.3) contacting the transfected cell population from step (6.2) with the first binding molecule which binds to the first gene product under conditions which allow the formation of complexes of first binding molecule and cells, and (6.4) separating said complexes of first binding molecule and cells from cells not bound to the binding molecule (negative cells), and optionally (6.5) repetition of the steps (6.1) to (6.4) at least one time, further preferably at least two times, further preferably at least three times, further preferably at least four times, and highly preferably at least five times.

This measure in connection with the "negative selection" occurs for the purpose of enrichment of the cells in which by homologous recombination an exchange of the coding nucleotide sequence for the first gene product against the coding nucleotide sequence for the second gene product has taken place. As the inventors were able to find out by the repeated carrying out of the steps (6.1) to (6.4) the cells which contain the recombinant expression vector are significantly enriched in only a short time so that the ratio of recombinant expression vectors to non-recombinant starting vectors is shifted in favor of the recombinant expression vectors. In this context, in step (6.5) an repetition for "at least" two, three, four, five times means that the steps (6.1) to (6.4) can also be repeated six, seven, eight, nine, ten times or even more often.

According to an embodiment of the method according to the invention after the step (7) the following further steps will follow:

(8) incubating the recombinant expression vectors with non-transfected cells under conditions which allow a transfection of the cells with the recombinant expression vectors, to obtain a further transfected cell population;

(9) contacting the further transfected cell population with the binding molecule that binds to the second gene product, under conditions which allow the formation of complexes of second binding molecule and second gene product, and

(10) separating the complexes of second binding molecule and second gene product, and optionally

(11) repeating the steps (8) to (10) at least one time, further preferably at least two times, further preferably at least three times, further preferably at least four times, and highly preferably at least five times.

This measure in connection with the "positive" selection is directed to the enrichment of such cells in a targeted manner, in which by homologous recombination an exchange of the coding nucleotide sequence for the first gene product against the coding nucleotide sequence for the second gene product hat taken place. Here it applies correspondingly what was mentioned for the enrichment steps (6.1) to (6.4) in connection with the "negative selection".

According to an embodiment of the method according to the invention the first and/or second binding molecule is an antibody.

This measure has the advantage that such binding molecules are employed which are particularly well suited for the method according to the invention.

In an embodiment of the method according to the invention the first and/or second binding molecule is bound to a magnetic entity.

This measure allows the applicability of the "magnetic cell separation" which is also referred to as "magnetic activated cell sorting" (MACS). The MACS technology is traditionally used to isolate cells which express a specific surface molecule or antigen. The binding molecules, such as antibodies are, in a preferred embodiment, bound to magnetic particles. These are generally approximately 50 nm large so-called "MicroBeads" which are routinely used in the context of MACS. They consist of iron oxide and an envelope of polysaccharides to which the binding molecules are bound. The cells expressing the first and/or second gene product are incubated with the magnetized binding molecules or the MicroBeads, respectively. The binding molecules find the first or second gene products, respectively, which may be cell-associated, i.e. are present in a complex with the cells. The binding molecules herewith provide for the binding of the MicroBeads to the corresponding cell population. In the flow of the entire cell population through a column which is surrounded by a strong magnetic field the cells complexed with the MicroBeads are retained. In doing so, by rinsing the column only non-complexed cells are obtained so that the complexed cell population is removed from the initial cell population. If in the context of the MACS system magnetic first binding molecules are used, the non-complexed cells are the target cells and it is referred to "negative selection" or reduction or depletion. If however magnetic second binding molecules are used the complexed cells are the target cells and it is referred to a "positive selection". The MACS system is well established and user-friendly and requires little technical expertise.

According to an embodiment of the method according to the invention the second gene product is an antigen, preferably a viral antigen, further preferably a tumor antigen or a tumor associated antigen, further preferably a viral tumor antigen or viral tumor associated antigen, and highly preferably a HPV selective viral tumor antigen or HPV selective viral tumor associated antigen.

Because of the short time of selection and the fast production process the method according to the invention provides optimum conditions to produce e.g. seasonal vaccines such as influenza vaccines, or individualized vaccines such as tumor vaccines. An "antigen" according to the invention refers to any nucleic acid encoded compound to which antibodies or lymphocyte receptors can bind. According to the invention such antigens are preferably included which are in connection with diseases such as infectious diseases or cancer. Of particular interest are also such antigens of the cottontail rabbit papilloma viruses (CRPV) or the human papilloma viruses (HPV), in particular such which can initiate tumors in an infected host.

According to an embodiment of the method according to the invention the starting vector is selected from:

virus derived vectors, including such which are derived from: pox viruses in particular *Parapoxvirus ovis* viruses (Orf viruses; ORFV) including the strain D1701; adeno associated viruses (AAV); adeno viruses, vaccinia viruses; baculo viruses; toga viruses; alpha viruses; arteri viruses; rubi viruses; influenza viruses; human papilloma viruses; herpes viruses, including CMV and RhCMV; arena viruses, including LCMV;

bacterial vectors including such which originate from: *Salmonella* sp., *Shigella* sp., *L. monocytogenesis, S. gordonii;* plasmids.

This measure has the advantage that such starting vectors are employed which are particularly well suited for the method according to the invention. The cell to be used, in which the starting vector should be introduced, results from the used starting vector. If the starting vector is a viral vector, according to the invention so-called permissive cells are used, which means cells in which after the introduction of the virus vector or the infection by the virus the entire reproduction cycle of the virus including the formation of infectious progeny viruses can take place. If for example an Orf virus (ORFV) is used as starting vector preferably kidney cells of the Vervet monkey, such as Vero cells, can be used as permissive cells. If plasmid vectors or plasmids are used according to the invention bacterial cells, e.g. such from *Escherichia coli*, can be employed.

Another subject matter of the present invention relates to a kit for the selection of recombinant expression vectors, comprising the following:

a starting vector encoding a first gene product, wherein the coding nucleotide sequence for the first gene product is upstreamly and downstreamly flanked by first recombination nucleotide sequences;

a transfer vector comprising a cloning side, wherein the cloning side is upstreamly and downstreamly flanked by second recombination nucleotide sequences which are homologous to the first recombination nucleotide sequences.

The first gene product is preferably a protein or protein fragment, further preferably a membrane protein, further preferably a cell surface protein, and highly preferably CD4.

The kit preferably further comprises a binding molecule that binds to the first gene product, further preferably an antibody, further preferably an antibody bound to a magnetic entity, and, optionally, a magnetic field column.

The kit according to the invention assembles the subjects required for carrying out the method according to the invention and, in that way, ensures a correct carrying out even by non-skilled personnel. It goes without saying that the kit according to the invention may also contain a manual for carrying out the method according to the invention and chemicals, salts, reagents, buffer etc.

The characteristics, features, and advantages of the method according to the invention apply to the kit according to the invention correspondingly.

Another subject matter of the present invention relates to a vector comprising a coding nucleotide sequence encoding a first gene product, which is upstreamly and downstreamly flanked by first recombination nucleotide sequences, wherein the first gene product is expressible in a cell in such a manner that it is accessible to a first binding molecule which binds to the first gene product. Here it is preferred if the first gene product is a protein or protein fragment, further preferably a membrane protein, further preferably a cell surface protein, and highly preferably CD4.

As a consequence, subject matter of the invention is also the starting vector that is used in the context of the method according to the invention, so that the features, advantages and characteristics of the method according to the invention, in particular of the starting vector, apply to the vector according to the invention correspondingly.

Against this background another subject matter of the present method also is a cell which contains the vector according to the invention.

The properties, features, and advantages of the cell or cell population used in the context of the method according to the invention apply likewise to the cell according to the invention.

Another subject matter of the present invention relates to the use of the vector according to the invention as starting vector and/or the cell according to the invention for the production of a recombinant expression vector which expresses an antigen, preferably a viral antigen, further preferably a tumor antigen or tumor associated antigen, further preferably a viral tumor antigen or viral tumor associated antigen, and highly preferably an HPV selective viral tumor antigen or HPV selective viral tumor associated antigen.

The features, advantages, and properties of the method according to the invention apply to the use according to the invention correspondingly.

It goes without saying that the before-mentioned features and those to be mentioned in the following cannot only be used in the respectively indicated combination but also in other combinations or in isolated position without departing from the scope of the present invention.

The invention is now further illustrated by means of embodiments which result in further features, properties, and advantages of the invention. The embodiments do not restrict the scope of the invention. It goes without saying that individual features of the embodiments can be used to specify, clarify, further develop or generalize the invention. In the embodiments reference is made to the enclosed figures.

EXAMPLES

Figure 1:
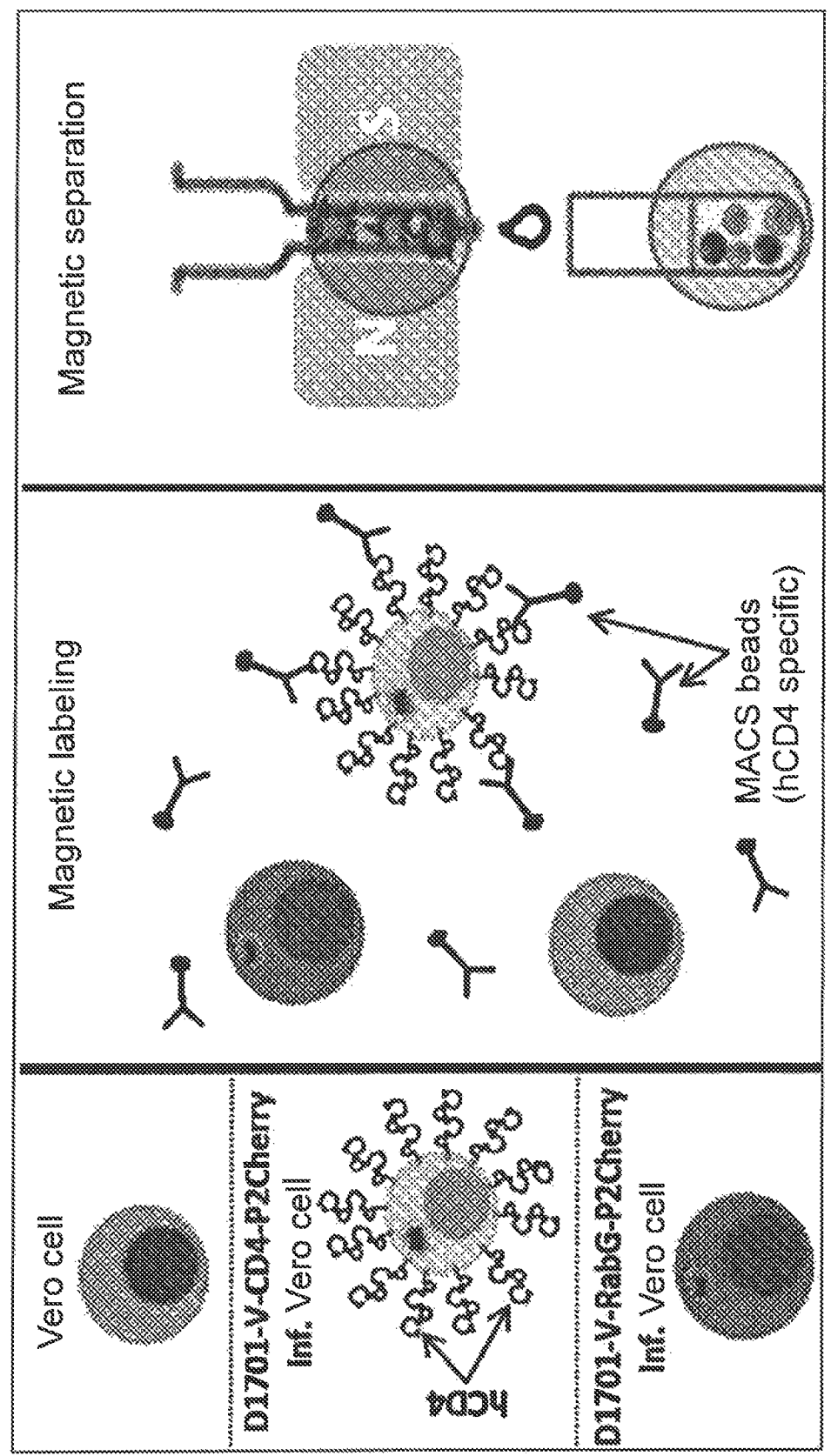
FIG. 1 schematic illustration of the MACS based selection.

1. New Selection Method for the Isolation of Recombinant Orf Viruses

Usually recombinant viruses such as pox viruses, are generated in permissive cells by means of homologous recombination of a transfer plasmid and the genome of the replicating virus. To ensure that the foreign DNA will be integrated into the desired position of the viral genome, the transfer plasmid contains homologous viral sequence sections which flank the foreign DNA to be inserted. Because recombination events occur very seldom, the recombination frequencies are usually between 1:1000 and 1:10.000, the selection of new recombinant viruses is mostly a quite difficult, expensive, and long lasting process which requires a high degree of technical know-how. As a result, different strategies were developed to facilitate a targeted selection of recombinant viruses. An interchangeable marker gene is often incorporated into the transfer plasmid and integrated into the viral genome together with the foreign gene or the "gene of interest". This technology has the decisive disadvantage that besides the foreign gene at the same time the marker gene is expressed in the recombinant viruses. Potential risks by an unwanted influence of the marker gene cannot be excluded and are in contradiction to a use that has to be approved. For this reason the production of marker-free recombinants is desirable. Different methods such as a visual selection by means of the expression of the β-galactosidase, β-glucuronidase or of fluorescence proteins and a transient "host range" selection, a transient dominant selection, or removable marker systems are described in the state of the art.

Often the common blue white selection is used for the production of recombinant Orf viruses, which is based on the hydrolysis of X-Gal by the β-galactosidase of the lacZ gene. However this method is very time-consuming and labor-intensive so that establishing a new more simple selection method is desirable.

For this reason in the first instance a fluorescence based selection method was developed wherein the lacZ gene was replaced by a fluorescence gene. New recombinants should be generated by replacing the fluorescence gene by a foreign gene and then visually selected via the loss of fluorescence.

Furthermore the method according to the invention was developed which, according to a preferred further development, is based on the use of the MACS technology.

The MACS technology is usually used to isolate cells which express a specific surface molecule or antigen. In this context advantage is taken of the fact that antibodies conjugated to magnetic particles, so-called MACS beads, specifically bind to cells and are retained in a strong magnetic field, thereby can be separated from nonbound cells. In connection with the works underlying the invention the recombinant D1701-V-CD4 was developed which expresses the human CD4 antigen (hCD4) and which should serve as starting recombinant for a MACS based selection. Because ORFV permissive Vero cells (monkey kidney cells) do not express hCD4, D1701-V-CD4 infected cells can be characterized by the surface expression of hCD4 and separated from noninfected cells by the aid of the MACS technology. In recombinants to be newly generated the exchange of the hCD4 by a foreign gene can now take place. Thereby in infected Vero cells the new hCD4 free recombinants can be easily separated from the parental hDC4 expressing viruses. This allows a technically essentially easier, more rapid and efficient selection of the desired new ORFV recombinants.

Important steps of the MACS based "negative" selection according to the invention are schematically shown in the FIG. 1. In this embodiment the first gene product or the selection marker is hCD4 and the second gene product or the "gene of interest" is the rabies virus glycoprotein (RabG). Further, a fluorescence protein named "Cherry" comes into play: The selection starts from a cell mixture obtained after the transfection, which contains non-infected Vero cells (medium grey), Vero cells infected with the starting recombinant D1701-V-CD4-P2Cherry and which express hCD4 (light grey), and Vero cells infected with the newly formed recombinant D1701-V-RabGP2Cherry (dark grey) (FIG. 1, left part). After the addition of hCD4 specific MACS beads conjugated with magnetic particles the antibodies bind to cells which express hDC4 at their surface (FIG. 1, middle part). The separation of the cell mixture is made by a column in a magnetic field. MACS beads coupled cells are retained in the magnetic field whereas non-bound cells can pass the magnetic field. In the flow, therefore, non-infected and the desired D1701-V-RabG-P2Cherry infected cells (hCD4 negative cell population: below, circled) are present, whereas in the column in the magnetic field D1701-V-hCD4P2Cherry infected cells accumulate (hCD4 positive cell population: top, circled) which are discarded (FIG. 1, right part).

2. Production and Characterization of the Starting Vector D1701-V-CD4-P2Cherry

Figure 2:
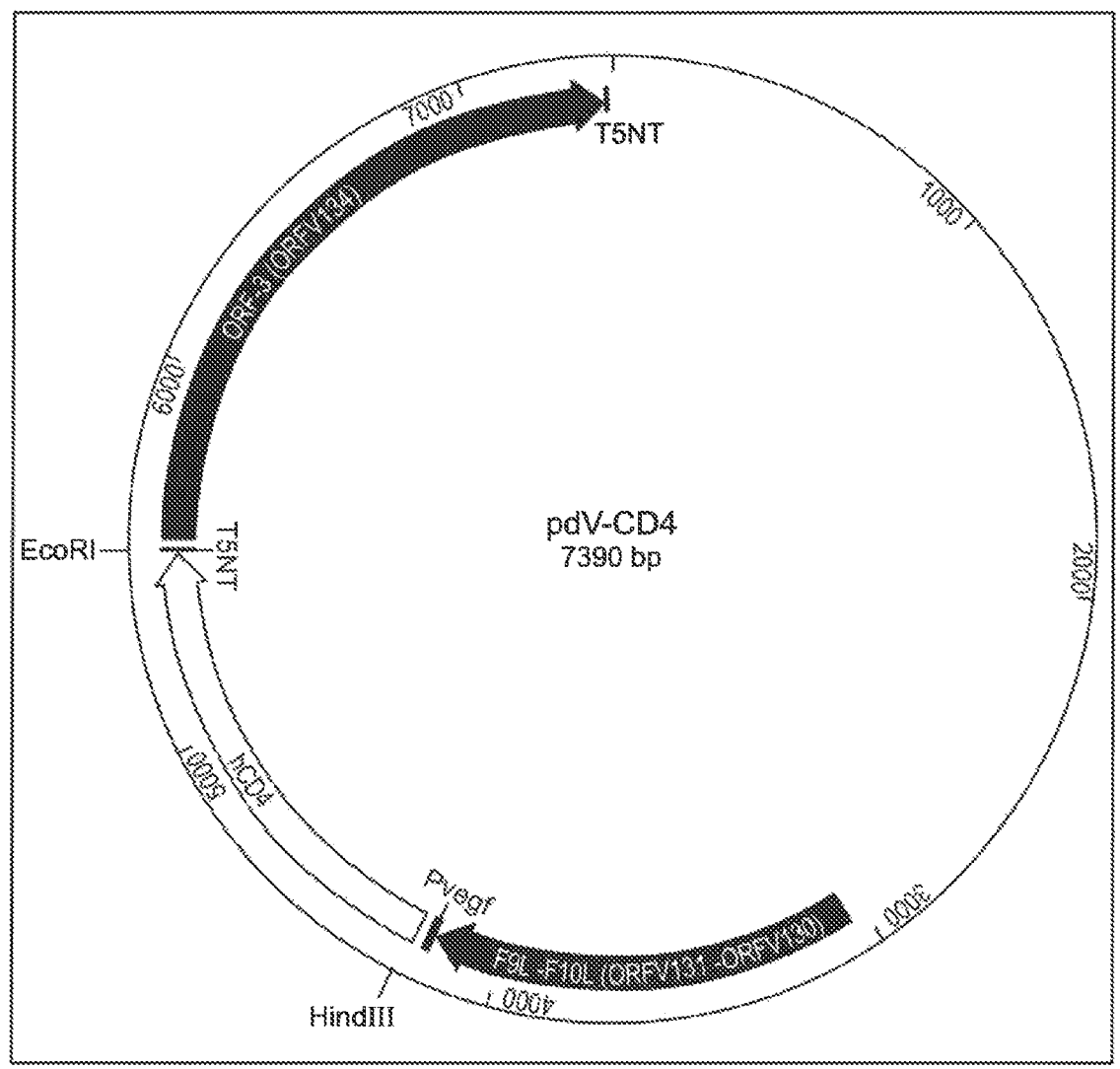
FIG. 2 schematic illustration of the transfer plasmid pdV-CD4.

The hDC4 gene sequence from pMACS 4.1 (Miltenyi) was chemically synthesized by the company Mr. Gene, Regensburg, Germany, and cloned into the plasmid pdV-Rec 1 via the restriction cleavage sites EcoRI and HindIII. The resulting transfer plasmid pdV-CD4 is schematically shown in the FIG. 2. There, the hCD4 gene is labeled in white. It is under the control of the original former promotor $P_{VEGF}$. The areas flanking the hCD4 gene which are shown in dark are downstreamly homologous to the ORFV genome area ORF-3 and upstreamly homologous to the ORFV genome area F9LF10L. These areas ensure a targeted integration of the hCD4 gene into the VEGF lokus of the D1701-V genome via homologous recombination. The restriction cleavage sites HindIII and EcoRI used for the cloning the pox specific early transcription stop motive T5NT are shown.

Figure 3:
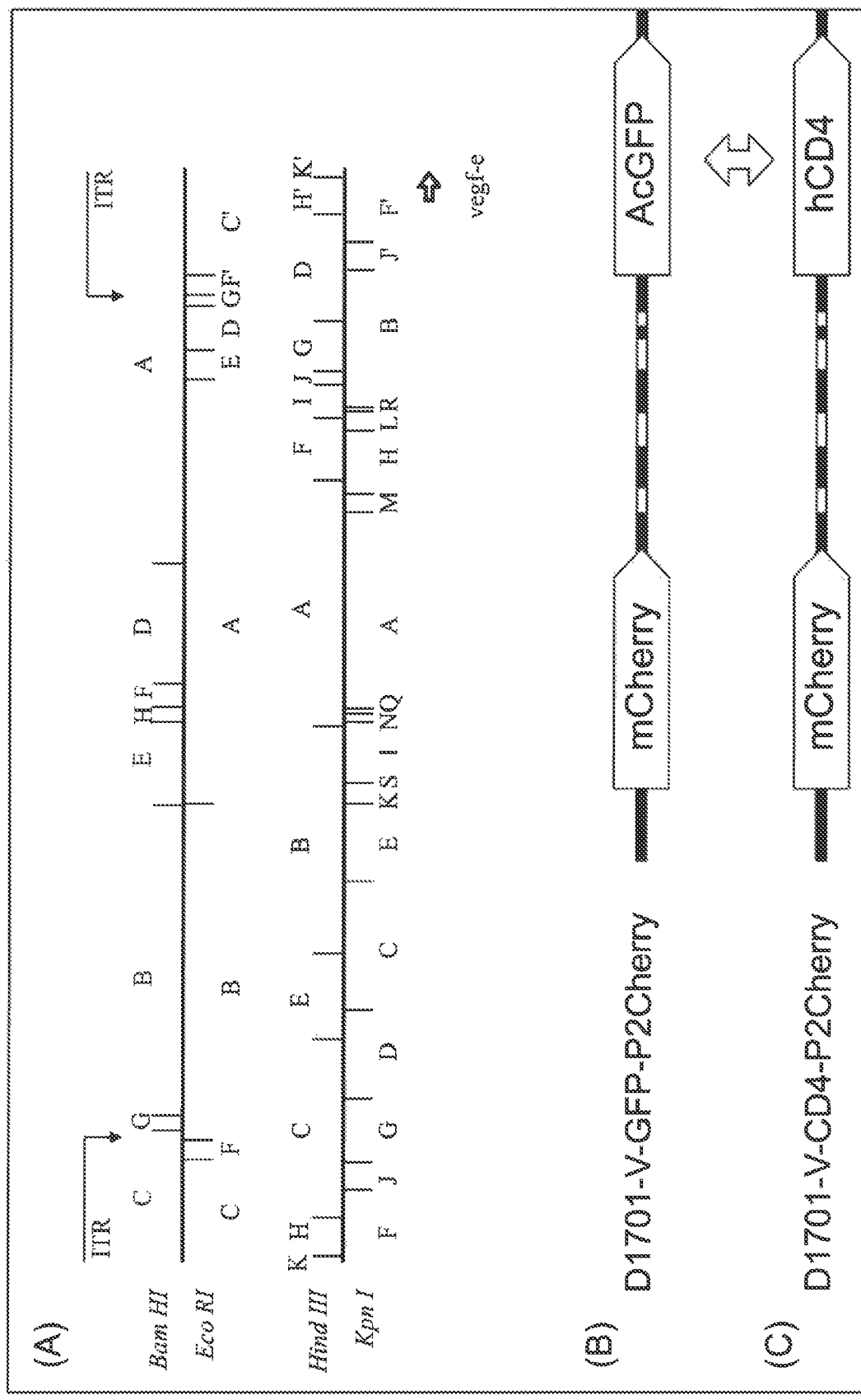
FIG. 3 production of the recombinant D1701-V-CD4-P2Cherry.

The newly resultant transfer plasmid pdV-CD4 was subsequently transfected into D1701-V-GFP-P2Cherry infected Vero cells, see FIG. 3. There in the partial FIG. 3A the restriction map of the D1701-V genome is shown. As shown in the partial FIG. 3B as the starting virus the double fluorescent recombinant D1701-V-GFP-P2Cherry was used (AcGFP="Aequorea coerulescens green fluorescent protein"); (mCherry="mCherry fluorescent protein). After the infection of Vero cells with the recombinant D1701-VGFP-P2Cherry the transfer plasmid pdV-CD4 (FIG. 2) was transfected into the cells by means of nucleofection. As shown in the partial FIG. 3C the generation of the initial vector D1701-V-CD4-P2Cherry is realized by integration of the hCD4 gene in exchange with the AcGFP-gene via homologous recombination.

New D1701-V-CD4-P2Cherry starting virus vectors can be distinguished and selected from the GFP-Cherry expressing parental virus vectors via the loss of GFP fluorescence. This is shown in the FIG. 4A: "loss of fluorescence": selection of D1701-VCD4-P2Cherry by means of fluorescence microscopy. Non-green fluorescent plaques (circled) were identified, picked and the virus was grown from the plaques. After five plaque purifications the homogeneity of D1701-V-CD4-P2Cherry could be assured via PCR analysis.

Figure 4:
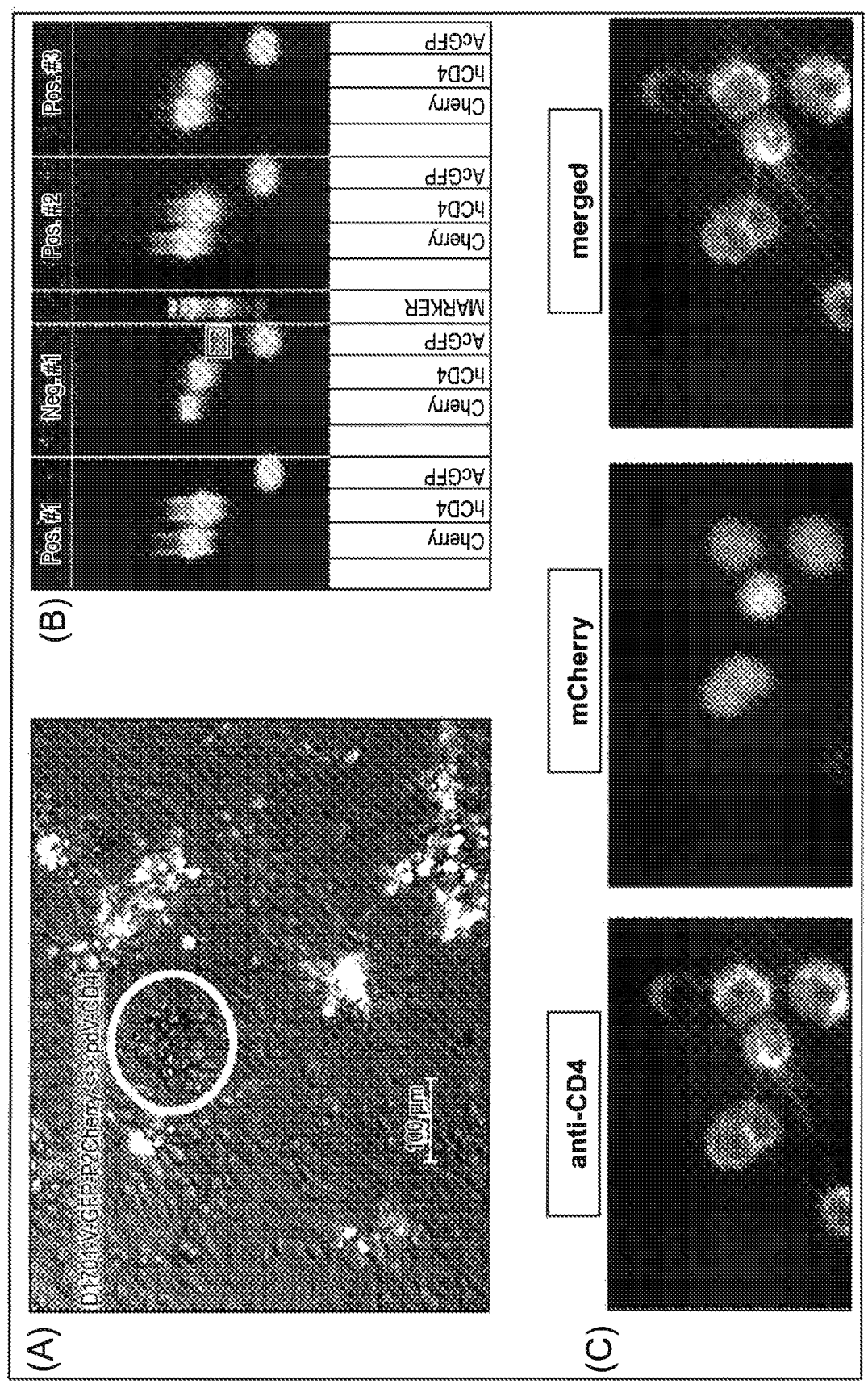
FIG. 4 selection of the recombinant D1701-V-CD4-P2Cherry.

The detection of the correct integration of the hCD4 gene in exchange with the AcGFP-gene in the VEGF lokus could be verified by means of specific PCR analysis and the genetic homogeneity of hCD4 positive and GFP negative ORFV recombinants was ensured, as shown in the FIG. 4B: exemplary PCR analysis after the fourth plaque purification. Recombinant D1701-V-CD4-P2Cherry is positive for the hCD4 gene and negative for the AcGFP gene contained in the starting recombinant. The detection was made via the indicated specific PCRs. The samples pos. #1-3 show homogenous recombinant starting virus vector with a specific hCD4 signal (Amplicon: 857 bp); neg. #1 shows a mixture of parental GFP containing (Amplicon: 575 bp) and recombinant CD4 containing starting virus vectors. The absence of the mCherry fluorescence gene was detected via a specific PCR (Amplicon: 1.103 bp).

Figure 5:
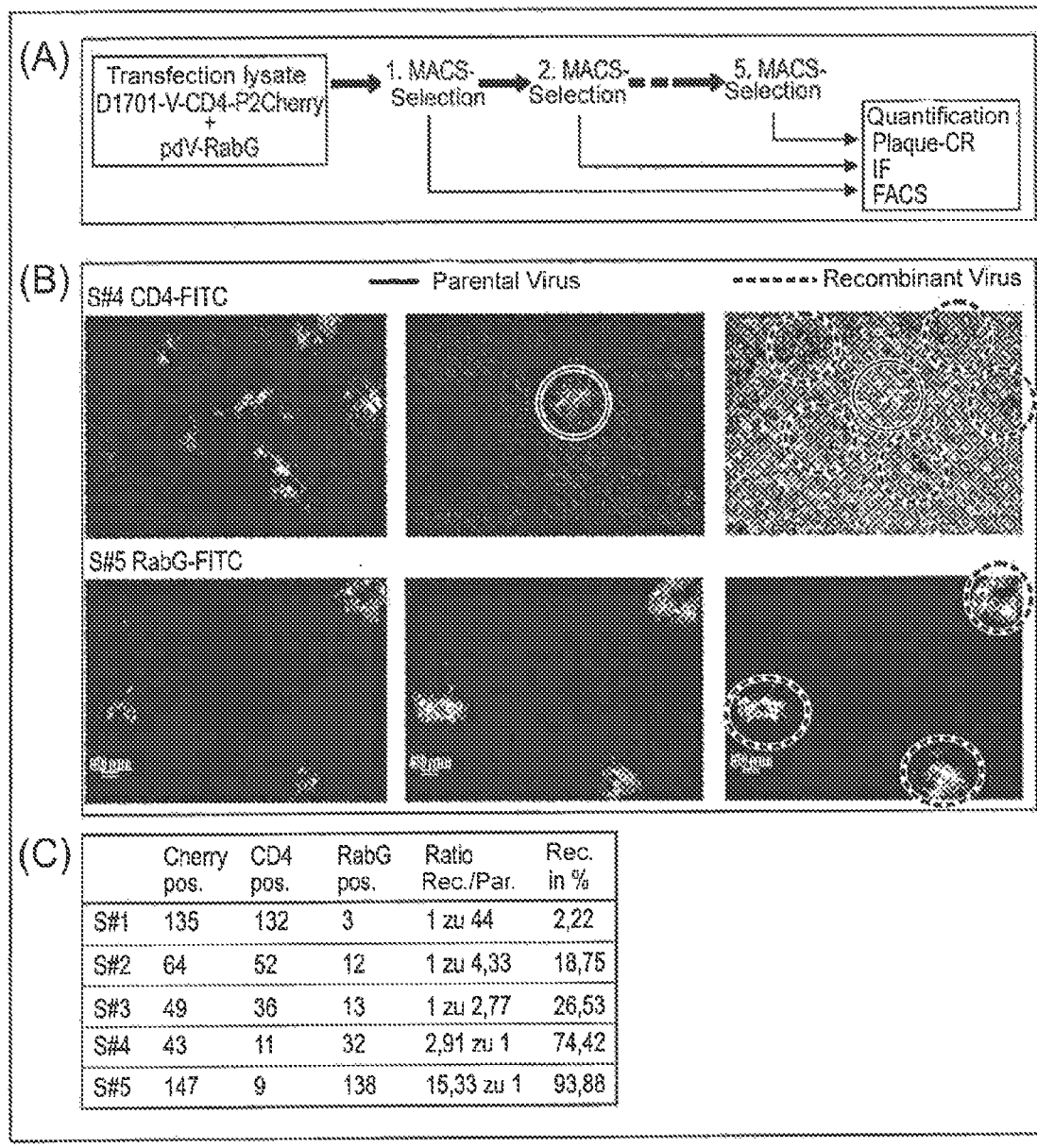
FIG. 5 MACS based selection oft he recombinant D1701-V-RabG-P2Cherry.
Figure 5:
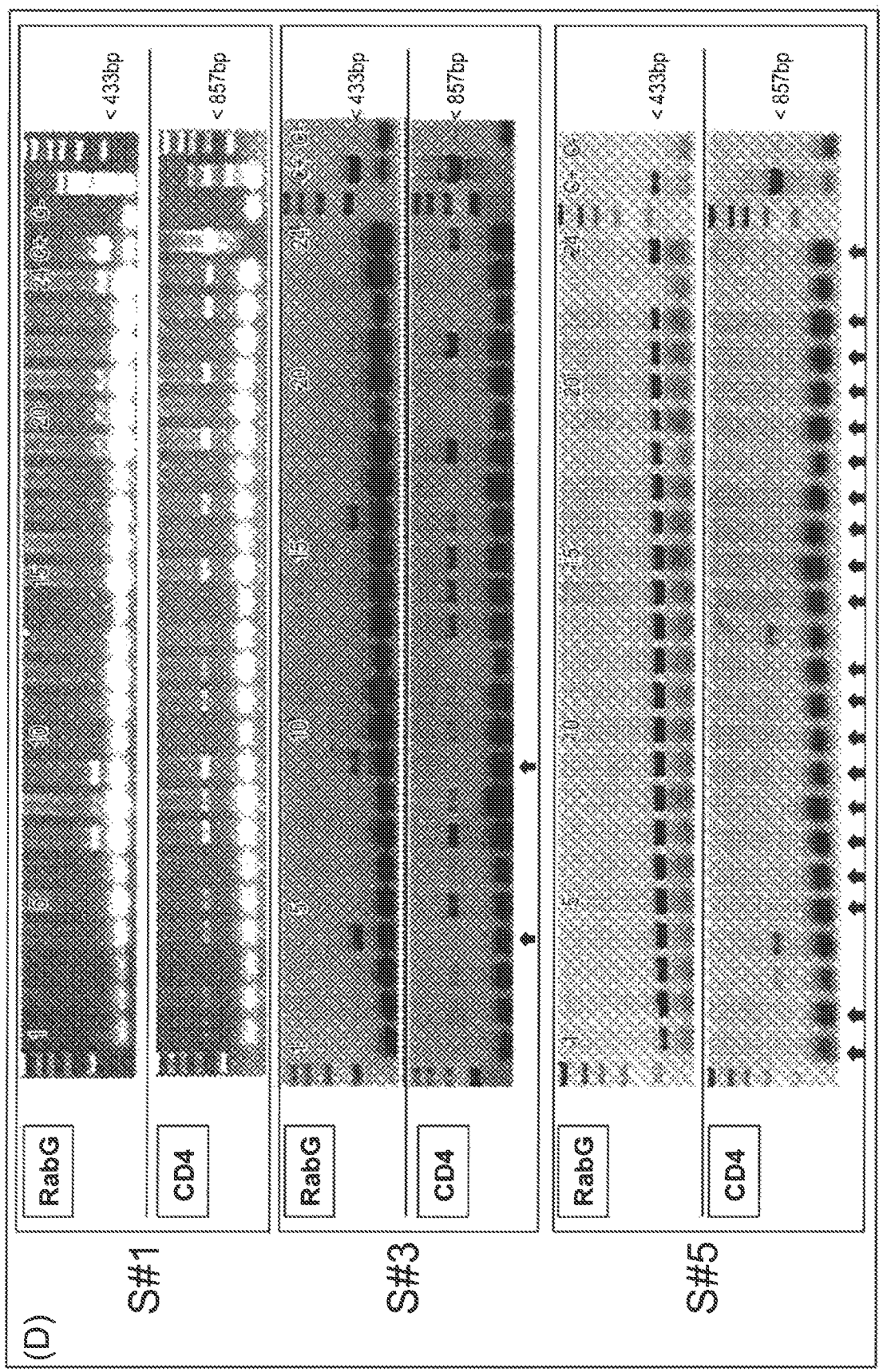

In the following the starting virus vector or the resulting recombinant virus was amplified in Vero cells and enriched via ultra centrifugation to high virus titers. The correct early expression of hCD4 in infected Vero cells was demonstrated via Western Blot analysis, immuno histochemical staining and immuno fluorescence analysis, as shown in FIG. 4C: immune fluorescence of D1701-V-CD4-P2Cherry infected Vero cells. Vero cells were infected with the initial vector D1701-V-CD4-P2Cherry. 20 hours after the infection the hCD4 protein was detected with a FITC conjugated anti CD4 antibody (Miltenyi). The fluorescence microscopy allows the illustration of the hCD4 surface expression ("anti-CD4"), the Cherry expression ("mCherry"), and both fluorescences in one cell after merger ("merged").

Growth kinetics of the cells which were transfected with the starting vector D1701-V-CD4-P2Cherry showed that the integration of the CD4 gene did not result in changes of the growth characteristics. The strength and the time course of the surface expression of CD4 in relation to the cell viability was determined by means of flow cytometry. There it could be found that already early after the transfection hCD4 is expressed on the surface of the cells and the intensity increases with progressing time. After approximately 20 to 24 hours first cytopathic effects can be seen and the cell viability decreases. Since released virus particles cannot be bound by MACS beads because of the lack of CD4 incoperation an infection period of 18 to 20 hours was established.

To obtain the most efficient separation of hCD4 positive and hCD4 negative cells in several pretests in addition different amounts of beads, incubation periods, temperatures and MACS columns were tested and the optimum selection conditions were established.

3. Generation of a New RabG Expressing Expression Vector D1701-V-RabG-P2Cherry by Means of MACS Selection In a next step by homologous recombination in the starting vector the coding nucleotide sequence for CD4 should be changed against the coding nucleotide sequence of a "gene of interest". The rabies virus glycoprotein (RabG) is the major antigen of the rabies virus (RV). RabG is expressed in the surface of RV and RV infected cells and is the target of virus neutralizing antibodies (VNA). The protection of an individual against rabies correlates with the level of the VNA titer. A recombinant virus or a recombinant expression vector which expresses RabG is for these reasons an appropriate tool for the production of a vaccine against the rabies virus. In this embodiment for this reason as a second gene product or "gene of interest" RabG is used.

D1701-V-CD4-P2Cherry infected Vero cells were incubated with the transfer plasmid pdV-RabG and incubated for 72 hours. After the disintegration of the viruses from the cell lysate fresh Vero cells were infected therewith. The cells were then incubated with CD4 specific MACS beads (Miltenyi) and separated by a magnetic column. hCD4 expressing cells infected with the starting vector D1701-V-CD4-P2Cherry remained in the magnetic field whereas the rest of the cells passed the column and gathered in the flow. Subsequently the hCD4 negative cell population was incubated for additional 20 hours at 37° C. and MACS selection was repeated. Altogether five of such rounds of MACS selection were carried out, whereas after each round a part of the negative cell population was used for the quantification of the efficiency of enrichment of new hCD4 negative recombinants; cf. FIG. 5A: schematic illustration of the experimental setup. After the transfection of D1701-V-CD4-P2Cherry infected Vero cells with the transfer plasmid pdV-RabG cells were incubated with the transfection lysate for 20 hours. CD4 negative cells (negative cell population) were isolated by MACS selection and after the addition of non-infected Vero cells incubated for additional 20 hours. At the same time a part of the negative cell population was used for the quantification of the efficiency of selection. In total 5 rounds of MACS selection were carried out.

The ratio of parental D1701-V-CD4-P2Cherry and newly generated recombinants 1701-V-RabG-P2Cherry was determined via single well PCR, fluorescence analysis and flow cytometry, as shown in the partial FIGS. 5A to 5B. FIG. 5B: evaluation of the efficiency of selection by means of hCD4- and RabG specific immune fluorescence staining. To determine the ratio of recombinant and parental virus after each round of selection cells of the negative population (FIG. 1, right part) were seeded into 6 well plates and 48 hours later either stained with hCD4 (exemplary illustration after the fourth round of MACS selection) or RabG specific (exemplary illustration after the fifth round of MACS selection) FITC coupled antibodies. Because all viruses express the Cherry fluorescence protein a simple distintion between parental and recombinant viruses is possible in the fluorescence microscope. In the top row (S#4 CD4-FITC) all parental viruses appear red green (continuous circle), whereas the recombinant viruses only shine in red (dashed circle); in the lower row (S#5 RabG-FITC) however recombinant viruses appear red green (dotted circled) and parental viruses are red. FIG. 5C: tabular overview of the efficiency of selection. The table shows exemplarily each proportion of parental and recombinant virus plaques after each of the five rounds of MACS selection which were carried out (S#1S#5). In addition the ratio of recombinant to parental virus plaques was determined (Ratio Rec./Par.) and the percentage of recombinant viruses resulting therefrom was calculated (Rec. in %). FIG. 5D: Identification of new MACS selected recombinants by means of PCR analysis. After each of the five rounds of MACS selection (S#1-S#5) cells of the negative population (FIG. 1, right part) were mixed in different ratios with non-infected Vero cells and seeded into 384 well plates. 72 hours after seeding wells where 1-5 individual plaques could be identified were harvested and the DNA was isolated. By means of hCD4 and RabG specific PCRs it was analyzed whether in the examined individual wells there was homogenous recombinant D1701-V-RabG-P2Cherry (e.g. S#5, lane 2; labeled by an arrow), homogenous parental 1701-V-CD4-P2Cherry (e.g. S#3, lane 15) or a mixture of both virus expression vectors (e.g. S#1, lane 8). The arrows represent wells which contain the new recombinant. The sizes of the respective PCR amplicons are indicated on the right in base pairs (bp).

Already after the third round of MACS selection individual wells could be found where the recombinant and thus the recombinant expression vector were present in a homogenous manner; see FIG. 5D. The virus culture of these homogenous D1701-VRabG-P2Cherry infected individual wells thereby allows the production of recombinant vectors already within one week. After the fourth round of selection D1701-V-RabGP2Cherry was already in superior number over the starting vector and another round of selection resulted in almost 95% of all viruses representing the new homogenous recombinant which expresses the RabG instead of the hCD4 gene; see FIG. 5B and 5C. These results could be confirmed by two further recombinants which were generated on the basis of the MACS selection system within 7 to 10 days.

4. Conclusion

Compared with the blue white selection which is usually used in the prior art and which takes approximately 3 month the selection process for the production of recombinant expression vectors by means of the method according to the invention could be accelerated by far, which besides time saving also results in lower costs. Because of the accelerated selection the method according to the invention now also provides excellent preconditions for the generation of vaccines which require a fast adaptation and/or production, such as seasonal vaccines, e.g. influenza virus vaccines or individualized vaccines, e.g. tumor vaccines. Another advantage is that the MACS system is well established and user friendly and for this reason requires little technical expertise. The described principle of selection is not only restricted to the exemplarily used Orf virus but facilitates and accelerates also the production of other recombinant expression vectors. Furthermore the new method can be used to positively select new recombinants which express a surface associated antigen by means of the use of specific MACS beads. The possibility to combine negative and positive selection as needed is another success-promising option.

What is claimed is:

1. A method for the production of recombinant expression vectors, comprising the following steps:
   (1) providing a cell population containing a starting vector, said cell population expresses a first gene product encoded by the starting vector, whereas in the starting vector the coding nucleotide sequence for the first gene product is upstreamly and downstreamly flanked by first recombination nucleotide sequences;
   (2) transfecting the cell population obtained from step (1) with a transfer vector encoding a second gene product, whereas in the transfer vector the coding nucleotide sequence for the second gene product is upstreamly and downstreamly flanked by second recombination nucleotide sequences which are homologous to said first recombination nucleotide sequences;
   (3) incubating the cell population obtained from step (2) under conditions which allow an exchange of the coding nucleotide sequence for said first gene product against the coding nucleotide sequence for said second gene product by homologous recombination of said first and second recombination nucleotide sequences and the formation of a recombinant expression vector;
   (4) incubating the cell population obtained from step (3) under conditions which allow the expression of said second gene product;
   (5) contacting the cell population obtained from step (4) with a first binding molecule that binds to said first gene product under conditions which allow the formation of complexes of said first binding molecule and said first gene product;
   (6) separating said complexes of first binding molecule and first gene product from the cell population;
   (7) isolating the recombinant expression vectors from the cell population;
   (8) incubating the recombinant expression vectors with non-transfected cells under conditions which allow a transfection of the non-transfected cells with said recombinant expression vectors to obtain a further transfected cell population;
   (9) contacting said further transfected cell population with a second binding molecule which binds to the second gene product under conditions which allow the formation a complexes of the second binding molecule and the second gene product;
   (10) separating said complexes of the second binding molecule and the second gene product; and
   (11) repeating the steps (8) to (10) at least one additional time.

2. The method of claim 1, wherein said first gene product is selected from the group consisting of protein, protein fragment, membrane protein, cell surface protein, and CD4.

3. The method of claim 2, wherein in step
   (5) the cell population obtained from step (4) is contacted with said first binding molecule which binds to said first gene product under conditions which allow the formation of complexes of first binding molecule and cell, and in step
   (6) said complexes of first binding molecule and cell are separated from cells which are not bound to said first binding molecule (negative cells), and in step
   (7) the recombinant expression vectors are isolated from the negative cells.

4. The method of claim 3, wherein after step (6) and before step (7) the following further steps occur:
   (6.1) disintegrating the negative cells to obtain a cell lysate containing said recombinant expression vectors
   (6.2) incubating the cell lysate obtained from step (6.1) with non-transfected cells under conditions which allow a transfection of the cells with the recombinant expression vectors, to obtain a transfected cell population;
   (6.3) contacting said transfected cell population obtained from step (6.2) with said first binding molecule which binds to the first gene product under conditions which allow the formation of complexes of first binding molecule and cell;
   (6.4) separating said complexes of first binding molecule and cell from cells which are not bound to the binding, molecule (negative cells); and
   (6.5) repeating the steps (6.1) to (6.4) at least one time.

5. The method of claim 1, wherein each of said first and said second binding molecule is an antibody.

6. The method of claim 5, wherein said second gene product is selected from the group consisting of antigen, viral antigen, tumor antigen, tumor associated antigen, viral tumor antigen, viral tumor associated antigen, HPV selective viral tumor antigen, and HPV selective viral tumor associated antigen.

7. The method of any of claim 1, wherein each of said first and second binding molecule is bound to a magnetic entity.

8. The method of claim 1, wherein the starting vector is selected from:
   virus derived vectors: virus vectors which derive from pox viruses, Parapoxvirus ovis viruses (ORFV), or ORFV D1701 strain; adeno associated viruses (AAV); adeno viruses; vaccinia viruses; baculo viruses; toga viruses; alpha viruses; arteri viruses; rubi viruses; influenza viruses; human papillama viruses; herpes viruses; CMV; RhCMV ; arena viruses; and LCMV;
   bacterial vectors: bacterial vectors which originate from *Salmonella* sp., *Shigella* sp., *L. monocytogenesis*, and *S. gordonii*; and
   plasmids.

9. The method of claim 1, wherein the second gene is a gene of interest and after step (11), a population of the recombinant expression vectors is obtained wherein about 95% of the recombinant expression vectors in the population are the recombinant expression vectors that express the second gene.

* * * * *